(12) United States Patent
Fujioka et al.

(10) Patent No.: US 8,216,206 B2
(45) Date of Patent: Jul. 10, 2012

(54) DISPOSABLE ABSORBENT ARTICLE

(75) Inventors: Masaru Fujioka, Tsurugi-cho (JP); Keiichi Ishikawa, Tsurugi-cho (JP)

(73) Assignee: Livedo Corporation, Shikokuchuo-shi (JP)

( * ) Notice: Subject to any disclaimer, the term of this patent is extended or adjusted under 35 U.S.C. 154(b) by 210 days.

(21) Appl. No.: 12/707,853

(22) Filed: Feb. 18, 2010

(65) Prior Publication Data

US 2010/0222756 A1    Sep. 2, 2010

(30) Foreign Application Priority Data

Feb. 27, 2009   (JP) ................................ 2009-045392

(51) Int. Cl.
    *A61F 13/15*    (2006.01)
(52) U.S. Cl. .......... 604/385.28; 604/385.29; 604/385.24
(58) Field of Classification Search ............. 604/385.28, 604/385.29, 385.3
    See application file for complete search history.

(56) References Cited

U.S. PATENT DOCUMENTS 5,662,637 A * 9/1997 Kitaoka et al. ........... 604/385.28

FOREIGN PATENT DOCUMENTS

JP           4-5825 U        1/1992

* cited by examiner

*Primary Examiner* — Jacqueline F. Stephens
(74) *Attorney, Agent, or Firm* — Westerman, Hattori, Daniels & Adrian, LLP (57) ABSTRACT

A disposable absorbent article comprising: an absorbent body including a top sheet, a back sheet and an absorbent core disposed therebetween; and a flap provided along an edge of opposite sides in a width direction of the absorbent core; wherein the flap has a fixing part joined to the top sheet and a rising part extending upward from the fixing part, and the rising part consists of a nonstretch nonwoven fabric which is water-repellent or liquid impermeable. Further, the flap may have a fold back part extending from the rising part and formed by folding back the rising part at an upper end of the rising part, wherein the fold back part consists of a nonstretch nonwoven fabric which is water-repellent or liquid impermeable, and the rising part and the fold back part are fusion-bonded to each other at a fusion-bond part.

9 Claims, 7 Drawing Sheets

DISPOSABLE ABSORBENT ARTICLE

BACKGROUND OF THE INVENTION

1. Field of the Invention

The present invention relates to a disposable absorbent article such as a sanitary napkin, a disposable diaper and the like.

2. Description of the Related Art

Conventionally, there is known a disposable absorbent article having a flap, and the flap is generally provided with an elastic member. For example, Japanese Laid-Open Utility Model Publication No. H4-5825 (Patent Document 1) discloses a disposable absorbent article having a flap which is provided with an elastic member. In Patent Document 1, though a plurality of elastic members are provided in the flap so as to be spaced from each other, no elastic member is provided at an upper end of the flap.

However, since the flap provided with the elastic member presses a wearer's skin at a part of the flap where the elastic member is disposed due to a elastic force of the elastic member, a feel of this part against the skin may become less comfortable. The present invention has been achieved in view of the above circumstances, and an object of the present invention is to provide a disposable absorbent article which has a flap whose pressure on a skin of the wearer is reduced as compared to that of a flap provided with an elastic member, thereby giving an excellent feeling to the wearer.

SUMMARY OF THE INVENTION

A disposable absorbent article of the present invention which solves the above problems comprises an absorbent body including a top sheet, a back sheet and an absorbent core disposed between the top sheet and the back sheet, and having a longitudinal direction and a width direction; and a flap provided along an edge of opposite sides in the width direction of the absorbent core; wherein the flap has a fixing part joined to the top sheet and a rising part extending upward from the fixing part, and the rising part consists of a nonstretch nonwoven fabric which is water-repellent or liquid impermeable. In the disposable absorbent article of the present invention, since the rising part of the flap consists of a nonstretch nonwoven fabric which is water-repellent or liquid impermeable, a pressure of the flap to a skin of a wearer is reduced as compared to that of a flap provided with an elastic member, resulting in giving an excellent feeling to the wearer.

Preferably, the flap has a fold back part extending from the rising part and formed by folding back the rising part at an upper end of the rising part, the fold back part consists of a nonstretch nonwoven fabric which is water-repellent or liquid impermeable, and the rising part and the fold back part are fusion-bonded to each other at a fusion-bond part. When the flap has the rising part and the fold back part which are fusion-bonded to each other at the fusion-bond part, rigidity is imparted to the flap due to the fusion-bond part. Therefore, even when the rising part and the fold back part are not provided with an elastic member, the flap is easily stabilized in a state of rising toward above the absorbent body. As a result, lateral leakage of urine and the like is easily prevented.

Preferably, the fusion-bond part is composed of a group of fusion-bonded lines aligned in the longitudinal direction, and each of the fusion-bonded lines has a shape of a continuous or discontinuous straight line arranged at an angle of from 45° to 135° to the upper end of the rising part. When the fusion-bond part is provided in such a manner, rigidity in a rising direction of the flap is imparted to the flap, resulting in improving stability of the flap in a rising state.

The disposable absorbent article may be a disposable diaper having a front part, a back part and a crotch part situated between the front part and the back part. In this case, the absorbent core is preferably provided at the crotch part, and an elastic member is preferably disposed so as to extend across the flap in the width direction in the crotch part. According to the disposable absorbent article defined as above, the elastic member disposed in the width direction in the crotch part acts so as to lift the crotch part of the absorbent body and the flap toward a wearer, thereby enhancing a fitting property of the flap to a wearer and preventing lateral leakage of urine and the like easily.

Both ends of the elastic member may extend along an edge of the crotch part of the disposable diaper. When both ends of the elastic member extend along an edge of the crotch part of the disposable diaper, leg elastic members around leg openings which a wearer steps into in wearing the diaper is formed, thereby preventing leakage of urine and the like through the leg openings easily. In addition, an elastic member can be easily provided at the crotch part and along the edge of the leg openings during production.

The rising part and/or the fold back part of the disposable absorbent article may have a colored portion having a shape of a linear or dots and disposed along the upper end of the rising part. The colored portion of the flap improves operability of wearing the disposable absorbent article and stacking an auxiliary absorbent article on the absorbent body, because the colored portion serves as a marker for the flap.

According to the disposable absorbent article of the present invention, a pressure of the flap to a skin of a wearer is reduced, resulting in giving an excellent feeling to the wearer.

DESCRIPTION OF THE PREFERRED EMBODIMENTS

A disposable absorbent article of the present invention comprises an absorbent body including a top sheet, a back sheet and an absorbent core disposed between the top sheet and the back sheet, and having a longitudinal direction and a width direction; and a flap provided along an edge of opposite sides in the width direction of the absorbent core. Examples of an embodiment of the disposable absorbent article of the present invention include a sanitary napkin, a disposable diaper and the like.

The absorbent body only needs to include the top sheet, the back sheet and the absorbent core between the top sheet and the back sheet. A shape of the absorbent body is not particularly limited as long as the absorbent body has a longitudinal direction and a width direction.

Examples of the shape of the absorbent body include a substantially rectangular shape, an hourglass shape and a center nipped-in gourd shape in the case that the disposable absorbent article is a sanitary napkin, for example.

In the case that the disposable absorbent article is a disposable diaper, for example, the disposable diaper preferably comprises a front part, a back part and a crotch part situated therebetween and provided with the absorbent core. When the disposable absorbent article is a disposable diaper, the disposable absorbent article may comprise a diaper main body which is formed from a laminate composed of an inner sheet and an outer sheet, and has a front part, a back part and a crotch part situated therebetween; and the absorbent body which includes the absorbent core and is provided at the crotch part, for example. In this case, examples of the shape of the absorbent body include a substantially rectangular shape. Also, when the disposable absorbent article is a disposable diaper, the disposable absorbent article may comprise the absorbent body having a front part, a back part and a crotch part situated therebetween; and the absorbent core provided at the crotch part, for example.

The longitudinal direction of the absorbent body means a direction extending in a front-back direction at a crotch of a wearer when the wearer wears the disposable absorbent article. When the shape of the absorbent body is a substantially rectangular shape, the longitudinal direction of the absorbent body is generally a long axis direction of the substantially rectangular shape (the direction in which a long side extends in the rectangular shape). When the shape of the absorbent body is an hourglass shape or a center nipped-in gourd shape, the longitudinal direction of the absorbent body is a direction extending across a constricted part of the each shape. When the absorbent body forms the front part, the back part and the crotch part, a direction from the front part toward the back part is the longitudinal direction. The width direction of the absorbent body means a direction orthogonal to the longitudinal direction in the same plane as the absorbent body.

Concerning names of the front part, the back part and the crotch part, a part applied to an abdomen side of a wearer is called the front part, a part applied to a buttocks side of the wearer is called the back part, and a part positioned between the front part and the back part and applied to a crotch of the wearer is called the crotch part, in a state of wearing the disposable diaper.

When the disposable absorbent article is the disposable diaper, the disposable diaper may be an open-type disposable diaper which is provided with a pair of fastening members on left and right sides of the back part or the front part and which is formed into a pants shape by using the fastening members when being worn, or the disposable diaper may be a pants-type disposable diaper in which the front part and the back part are joined to each other to form a waist opening and a pair of leg openings.

The top sheet is preferably liquid-permeable, and the back sheet is preferably liquid-impermeable or water-repellent. The inner sheet is preferably hydrophilic or water-repellent, and the outer sheet is preferably water-repellent.

The absorbent core is not particularly limited as long as it absorbs excrement such as urine and the like, however, it preferably contains an absorbent resin. The absorbent core can be obtained, for example, by the steps of mixing a hydrophilic fiber assembly such as crushed pulp fibers, cellulose fibers and the like with a granular absorbent resin to obtain a clump; wrapping the clump with a paper sheet such as a tissue paper and the like, or with a cover sheet such as a liquid-permeable nonwoven fabric sheet and the like; and molding the obtained wrapped clump into a predefined shape such as a rectangular shape, a hourglass shape, a center nipped-in gourd shape, a battledore shape, and the like.

The disposable absorbent article of the present invention comprises a flap provided along an edge of opposite sides in the width direction of the absorbent core, and the flap has a fixing part joined to the top sheet and a rising part extending upward from the fixing part. A position where the flap is provided is not particularly limited as long as the flap is provided along the edge of opposite sides in the width direction of the absorbent core. For example, the flaps may be provided on an upper surface of the absorbent core at both ends thereof in the width direction, or provided at outward in the width direction of the absorbent core. However, a boundary between the fixing part and the rising part of the flap is located preferably in a region within 20 mm inward or outward in the width direction from the edges of opposite sides in the width direction of the absorbent core.

The fixing part of the flap only needs to be joined to at least the top sheet, and may be also joined to a part other than the top sheet, such as the back sheet.

The rising part of the flap extends upward from the fixing part. The term "upward" means a direction which is orthogonal to the longitudinal direction and the width direction of the absorbent body and which extends from the absorbent body toward a wearer. The rising part consists of a nonstretch nonwoven fabric which is water-repellent or liquid impermeable. Thus, the rising part is not provided with an elastic member or the like. In the disposable absorbent article of the present invention, since the rising part of the flap consists of a nonstretch nonwoven fabric which is water-repellent or liquid impermeable, a pressure of the flap to a skin of a wearer is reduced as compared to that of a flap provided with an elastic member, resulting in giving an excellent feeling to the wearer.

Figure 1:
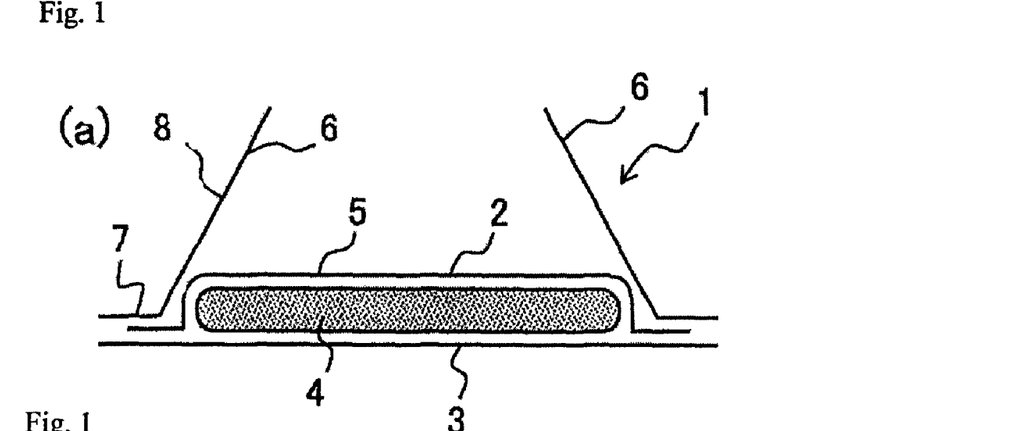
FIG. 1(a) to (c) show examples of width direction cross-sectional views of an absorbent body and a flap of the disposable absorbent article of the present invention.

FIG. 1 shows embodiments of a flap provided in a disposable absorbent article of the present invention. FIG. 1 shows width direction cross-sectional views of an absorbent body and the flap of the disposable absorbent article of the present invention.

In FIG. 1(a), a disposable absorbent article 1 comprises an absorbent body 5 including a top sheet 2, a back sheet 3 and an absorbent core 4 disposed between the top sheet 2 and the back sheet 3, and having a longitudinal direction and a width direction x; and flaps 6 provided along an edge of opposite sides in the width direction x of the absorbent core 4. The flap 6 has a fixing part 7 joined to the top sheet 2. The flap 6 further has a rising part 8 which extends upward z1 from the fixing part 7. The rising part 8 of the flap 6 is not provided with an elastic member or the like.

In FIG. 1(b), the rising part 8 of the flap 6 extends upward z1 from the fixing part 7, and the flap 6 is folded back at an upper end 9 of the rising part 8. The flap 6 has a fold back part 10 extending from the rising part 8 and formed by folding back the rising part 8 at the upper end 9 of the rising part 8. When the flap 6 has the fold back part 10, the fold back part 10 consists of a nonstretch nonwoven fabric which is water-repellent or liquid impermeable, similarly to the rising part 8. In the case that the flap 6 has the fold back part 10, the rising part 8 and the fold back part 10 are fusion-bonded to each other at a fusion-bond part 11. When the flap 6 has the rising part 8 and the fold back part 10 which are fusion-bonded to each other at the fusion-bond part 11, rigidity is imparted to the flap 6 due to the fusion-bond part 11. Therefore, even when the rising part 8 and the fold back part 10 are not provided with an elastic member, the flap 6 is easily stabilized in a state of rising toward above the absorbent body 5. As a result, lateral leakage of urine and the like is easily prevented.

In FIG. 1(*b*), the rising part 8 of the flap 6 is folded back inward in the width direction at the upper end 9. However, as shown in FIG. 1(*c*), the rising part 8 of the flap 6 may be folded back outward in the width direction at the upper end 9. Further, as shown in FIG. 1(*c*), the fold back part 10, which is formed by folding back the rising part 8 at the upper end 9, may be joined to the absorbent body 5. When the fold back part 10 is joined to the absorbent body 5, the flap 6 rises upward more easily.

The fusion-bond part provided in the flap is preferably composed of a group of fusion-bonded lines aligned in the longitudinal direction, and each of the fusion-bonded lines preferably has a shape of a continuous or discontinuous straight line arranged at an angle of from 45° to 135° to the upper end of the rising part. When the fusion-bond part is provided in such a manner, rigidity is imparted to the flap in a rising direction, resulting in improving stability of the flap in a rising state.

The fusion-bond part may be formed by heat-sealing (thermal-fusion-bonding) the nonwoven fabrics, which respectively form the rising part and the fold back part, with a predetermined pattern in a state that the flap is folded so as to form the rising part and the fold back part of the flap.

Figure 2:
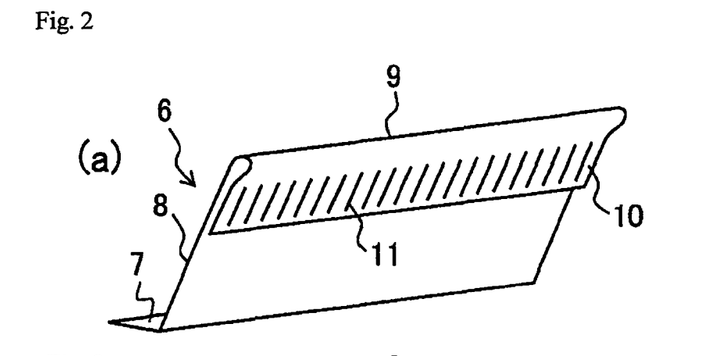
FIG. 2(a) to (d) show examples of a fusion-bond part which is provided in a flap of a disposable absorbent article of the present invention.

Examples of an embodiment of the fusion-bond part will be described referring to FIG. 2. FIG. 2 shows examples of the fusion-bond part which is provided in the flap shown in FIG. 1(*b*).

In FIG. 2(*a*), the fusion-bond part 11 is composed of a group of fusion-bonded lines aligned in the longitudinal direction y, and each of the fusion-bonded lines has a shape of a continuous straight line arranged at an angle of 90° to the upper end 9 of the rising part 8. When the fusion-bond part 11 is provided in the flap 6 as shown in FIG. 2(*a*), rigidity in the rising direction is imparted to the flap, resulting in improving stability of the flap in the rising state.

In FIG. 2(*b*), the fusion-bond part 11 is composed of a group of fusion-bonded lines aligned in the longitudinal direction y, and each of the fusion-bonded lines has a shape of a continuous straight line arranged at an angle of 90° to the upper end 9 of the rising part 8, however, the fusion-bonded lines are provided only at and near a center of the flap in the longitudinal direction y. When the fusion-bond part 11 is provided in the flap 6 as shown in FIG. 2(*b*), rigidity in the rising direction is imparted only to and near the center of the flap in the longitudinal direction y. Therefore, the flap rises at and near the center thereof in the longitudinal direction y more stably than at ends thereof in the longitudinal direction y, thereby naturally forming a leakage-preventing wall about a center of the crotch part.

In FIG. 2(*c*), the fusion-bond part 11 is composed of a group of fusion-bonded lines aligned in the longitudinal direction y, and each of the fusion-bonded lines has a shape of a continuous straight line arranged at an angle of from 45° to 135° to the upper end 9 of the rising part 8. In FIG. 2(*c*), the group of the fusion-bonded lines is aligned so as to be inclined toward the center of the flap in the longitudinal direction y. When the fusion-bond part 11 is provided in the flap 6 as shown in FIG. 2(*c*), stability of the flap in the longitudinal direction y in the rising state improves.

In FIG. 2(*d*), the fusion-bond part 11 is composed of a group of fusion-bonded lines aligned in the longitudinal direction y, and each of the fusion-bonded lines has a shape of a discontinuous straight line. Specifically, fusion-bonded lines arranged at an angle of from 45° to 90° to the upper end 9 of the rising part 8 and fusion-bonded lines arranged at an angle of from 90° to 135° to the upper end 9 of the rising part 8 are alternately aligned. As shown in FIG. 2(*d*), each of the fusion-bonded lines may have a shape of a discontinuous straight line. Providing the fusion-bonded lines in a zigzag manner as shown in FIG. 2(*d*) improves stability of the flap in the longitudinal direction y in the rising state.

The group of the fusion-bonded lines which forms the fusion-bond part is preferably composed of 5 or more fusion-bonded lines, more preferably 8 or more fusion-bonded lines, and even more preferably 12 or more fusion-bonded lines. When the group of the fusion-bonded lines is composed of 5 or more fusion-bonded lines, rigidity in the rising direction is imparted to the flap easily, resulting in improving stability of the flap in the rising state.

A length of each fusion-bonded line in the group of the fusion-bonded lines which forms the fusion-bond part is preferably 1 mm or more, more preferably 3 mm or more, and even more preferably 5 mm or more. When the length of the each fusion-bonded line is equal to or greater than 1 mm and each fusion-bonded line is arranged at the angle of from 45° to 135° to the upper end of the rising part, rigidity in the rising direction is easily imparted to the flap, resulting in improving stability of the flap in the rising state. An upper limit of the length of the each fusion-bonded line is not particularly limited as long as each fusion-bonded line is provided in both the rising part and the fold back part.

The fusion-bonded lines do not need to be arranged at equal intervals. Preferably, the group of the fusion-bonded lines is provided in a central region which covers 50% of the flap in the longitudinal direction, that is in a region corresponding to two middle parts of the flap which has been divided into four equal parts in the longitudinal direction. More preferably, the group of the fusion-bonded lines is provided in a central region which covers 33% of the flap in the longitudinal direction, that is in a region corresponding to a middle part of the flap which has been divided into three equal parts in the longitudinal direction. When the group of the fusion-bonded lines is provided in the flap at the central region in the longitudinal direction, the flap rises at and near a center thereof in the longitudinal direction more stably than at ends thereof in the longitudinal direction, thereby forming a leakage-preventing wall around a center of the crotch part naturally.

The rising part and/or the fold back part of the flap may have a colored portion having a shape of a linear or dots and disposed along the upper end of the rising part. The colored portion along the upper end of the rising part of the flap facilitates wearing of the disposable absorbent article such that the flap extends along inguinal regions of a wearer, because the colored portion serves as a marker for the flap. In addition, operability of overlapping an auxiliary absorbent article such as an urinary incontinence pad between the two flaps is improved.

The colored portion is preferably not disposed at the upper end of the rising part. When the colored portion is disposed at the upper end of the rising part, the colored portion come to be disposed at a relatively angular part of the upper end, and this part is likely to strongly contact a wearer's skin, causing the possibility that the skin is stained. Therefore, the colored portion is disposed in the rising part and/or the fold back part. In order for the colored portion to serve as a marker for the flap, the colored portion is preferably disposed on an outer side in the width direction of the flap along the upper end of the rising part. In addition, in order for the colored portion to serve as a marker for the flap, the colored portion is preferably disposed in a region within 10 mm from the upper end of the rising part.

Figure 3A:
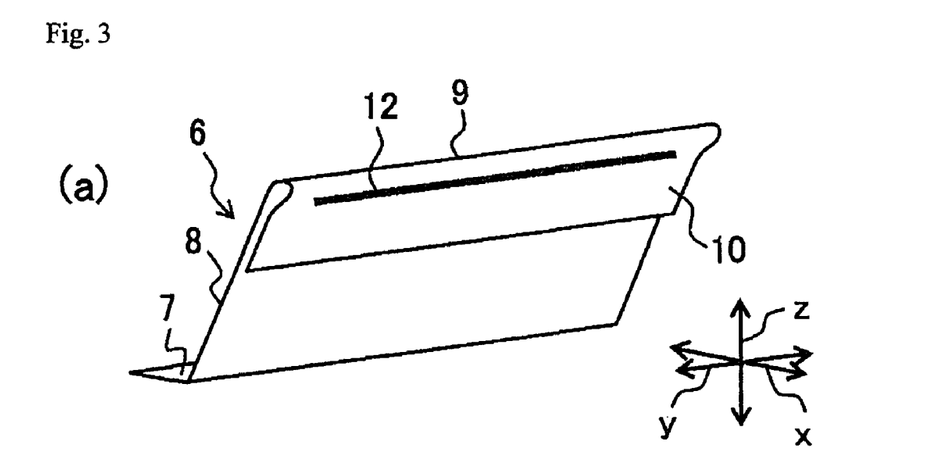
FIG. 3(a) to (b) show examples of a colored portion which is provided in a flap of a disposable absorbent article of the present invention.
Figure 3B:
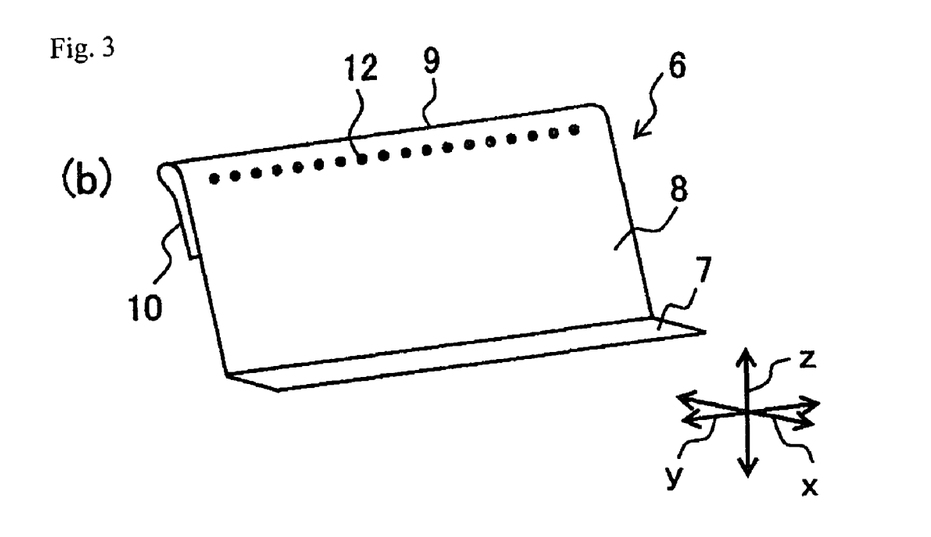

Examples of an embodiment of the colored portion will be described referring to FIG. 3. FIG. 3 shows examples of the colored portion which is provided in the flap shown in FIG. 1(b). In FIG. 3(a), the fold back part 10 has a colored portion 12 having a shape of a linear and disposed along the upper end 9 of the rising part 8. In FIG. 3(b), the rising part 8 has a colored portion 12 having a shape of dots and disposed along the upper end 9 of the rising part 8.

The nonwoven fabric constituting the flap is not limited as long as it is water-repellent or liquid-impermeable.

The nonwoven fabric constituting the flap is preferably a nonwoven fabric manufactured by a spunbond method, an air-through method, a point bonding method, a melt blowing method, an airlaid method, a combination of these methods, or the like. Further, a nonwoven fabric manufactured by the spunbond method or a SMS method which is a combination of the spunbond method and the melt blowing method is preferable, and a nonwoven fabric manufactured by the spunbond method is especially preferable. By using such a nonwoven fabric, the flap with high strength is easily obtained.

A material of the nonwoven fabric which forms the flap can be selected as appropriate from synthetic fibers such as polypropylene, polyethylene, polyester, and polyamide; and natural fibers such as pulp and silk. The nonwoven fabric may be formed from a water-repellent or liquid impermeable fiber, or the nonwoven fabric may be formed from a hydrophilic fiber and a surface thereof may be subjected to a water-repellent or liquid impermeable treatment. Among them, thermoplastic synthetic fibers such as polypropylene, polyethylene, and polyester are preferable, polypropylene fibers and polyester fibers are more preferable, and polypropylene fibers are even more preferable. When a nonwoven fabric obtained from such a material is used, a high-rigidity flap is easily obtained, and the fusion-bond part is easily formed in the flap.

The nonwoven fabric constituting the flap has preferably a mass per unit area of 5 $g/m^2$ or more, more preferably 10 $g/m^2$ or more, preferably 50 $g/m^2$ or less, and more preferably 35 $g/m^2$ or less. When the nonwoven fabric having a mass per unit area in the range of from 5 $g/m^2$ to 50 $g/m^2$ is used, breathability of the nonwoven fabric is easily ensured and elasticity of the nonwoven fabric is easily obtained. Therefore, the flap made of such a nonwoven fabric is gentle to a skin, improves comfort for a wearer, and further does not easily bend, resulting in easily forming a leakage-preventing wall.

The disposable absorbent article of the present invention is preferably a disposable diaper having the front part, the back part and the crotch part situated between the front part and the back part, wherein the absorbent core is provided at the crotch part, and an elastic member is disposed so as to extend across the flap in the width direction in the crotch part. The disposable diaper may be an open-type disposable diaper which is formed into a pants shape in wearing the disposable diaper, or may be a pants-type disposable diaper which has a waist opening and a pair of leg openings formed by joining the front part and the back part.

The crotch part of the disposable diaper is a middle position provided with cutouts, which is intended to form leg openings, when the diaper is divided into three parts, that is the front part, the back part and the crotch part, in a longitudinal direction of the diaper in a state that the diaper is developed on a plane.

The absorbent core is provided at the crotch part. The disposable diaper may comprise a diaper main body having the front part, the back part and the crotch part, and the absorbent body in which the absorbent core is provided between the top sheet and the back sheet, wherein the absorbent body is provided at the crotch part of the diaper main body. The disposable diaper may also comprise the absorbent body, in which the absorbent core is provided between the top sheet and the back sheet, having the front part, the back part and the crotch part, and the absorbent core provided at the crotch part of the absorbent body.

In the crotch part of the disposable diaper, a crotch elastic member may be disposed so as to extend in the width direction across the two flaps which are provided along each edge of opposite sides in the width direction of the absorbent core. When the crotch elastic member is disposed, the crotch part of the absorbent body and the flap are lifted toward a wearer due to a shrinkage force of the crotch elastic member in wearing the disposable diaper, resulting in enhancing a fitting property of the flap to the wearer and preventing lateral leakage of urine and the like easily.

The crotch elastic member is preferably disposed so as to extend continuously and linearly in the width direction in the crotch part. When the crotch elastic member is disposed in such a manner, the effect of lifting the crotch part of the absorbent body and the flap is exerted further.

The crotch elastic member may be composed of either one elastic member or a plurality of elastic members. In the case that the crotch elastic member is composed of a plurality of elastic members, the respective elastic members are preferably aligned substantially parallel to each other. In addition, in the case that the crotch elastic member is composed of a plurality of elastic members, intervals between the adjacent elastic members are preferably substantially the same. When the elastic members constituting the crotch elastic member are aligned substantially parallel to each other, the elastic force of the crotch elastic member is exerted at its maximum. When the intervals between the adjacent elastic members constituting the crotch elastic member are substantially the same, the elastic force is evenly exerted at a region where the crotch elastic member is disposed at the crotch part, thereby improving the fitting property of the flap to a wearer.

A number of the elastic member constituting the crotch elastic member is preferably 1 or more, more preferably 2 or more, and even more preferably 3 or more, and preferably 10 or less, more preferably 8 or less, and even more preferably 6 or less. When the number of the elastic member constituting the crotch elastic member is 1 or more, the fitting property of the flap to a wearer is improved. On the other hand, when the number of the elastic member constituting the crotch elastic member exceeds 10, the effect due to the crotch elastic member is not improved markedly and the production becomes difficult to increase a production cost. Therefore, the number of the elastic member constituting the crotch elastic member is preferably 10 or less.

In the case that the crotch elastic member is composed of a plurality of elastic members, a distance between a frontmost elastic member and a rearmost elastic member in the longitudinal direction is preferably 105 mm or less, and more preferably 80 mm or less. When the distance between the frontmost elastic member and the rearmost elastic member is 105 mm or less, the fitting property of the flap to a wearer at the crotch part is easily improved. A lower limit of the distance between the frontmost elastic member and the rearmost elastic member is not restricted particularly, however, the distance is preferably 0.5 mm or more, and more preferably 1 mm or more from a viewpoint of easily placing of the elastic members. Here, in the case that the distance between the frontmost elastic member and the rearmost elastic member means varies according to a measurement point, the distance means the shortest distance between the frontmost elastic member and the rearmost elastic member.

Both ends of the crotch elastic member may extend along an edge of the crotch part. Both ends of the crotch elastic member extending along the edge of the crotch part forms leg elastic members around the leg openings which a wearer steps into in wearing the diaper. When the both ends of the crotch elastic member extend along the edge of the crotch part to form the leg elastic members, leakage of urine and the like through the leg openings is easily prevented. In addition, the crotch elastic member and the leg elastic member can be easily provided during production.

Preferably, the crotch elastic member is composed of a plurality of elastic members, both ends of at least one of the crotch elastic members extend along the edge of the crotch part on a front side (on the front side when the diaper is worn), and both ends of at least another one of the crotch elastic members extend along the edge of the crotch part on a back side (on the back side when the diaper is worn). When the elastic members are provided in such a manner, the elastic members are provided substantially along an entire circumferences of the leg openings, thereby preventing leakage of urine and the like through the leg openings more assuredly.

The disposable diaper may further comprise a waist elastic member disposed along an edge of the waist opening, or a body elastic member disposed in the front part and the back part so as to extend in the width direction. The waist elastic member prevents excrement such as urine and the like from leaking from a back side or an abdomen side, even when a wearer lies. The body elastic member improves the fitting property of the diaper around an abdomen region.

Elastic materials such as a polyurethane thread, a polyurethane film, a natural rubber and the like, which are generally used for disposable diapers, can be used for respective elastic members. The respective elastic members are preferably attached in a stretched state on a sheet or between sheets by bonding means such as a hot-melt adhesive agent, a heat bonding, an ultrasonic bonding, and the like. For example, a polyurethane thread having a fineness of 100 dtex to 2,500 dtex is stretched at a ratio of 1.1 to 5.0 times to be fixed. The preferable bonding means is a rubber-based hot-melt adhesive agent.

Respective elastic members mounted to the disposable diaper are preferably disposed between two sheets. For example, in the case that the disposable diaper comprises the diaper main body having the front part, the back part and the crotch part, and the absorbent body in which the absorbent core is provided between the top sheet and the back sheet, the diaper main body is preferably formed from the laminate composed of the inner sheet and the outer sheet, and the respective elastic members are preferably disposed between the inner sheet and the outer sheet. Here, the absorbent body may not be joined to a part of the diaper main body where the crotch elastic member is disposed. When the absorbent body is not joined to the part of the diaper main body where the crotch elastic member is disposed, an elastic force in the width direction of the crotch elastic member is not prevented by a rigidity of the absorbent core, thereby improving the effect of lifting the crotch part of the absorbent body and the flap.

For example, in the case that the disposable diaper comprise the absorbent body, in which the absorbent core is disposed between the top sheet and the back sheet, having the front part, the back part and the crotch part, the respective elastic members are preferably disposed between the top sheet and the back sheet. At a part of the absorbent body where the absorbent core is disposed, the respective elastic members are disposed preferably between the absorbent core and the back sheet. In this case, the crotch elastic member may not be joined to the absorbent core. When the crotch elastic member is not joined to the absorbent core, an elastic force in the width direction of the crotch elastic member is not prevented by a rigidity of the absorbent core, thereby improving the effect of lifting the crotch part of the absorbent body and the flap.

Next, an example of the disposable diaper (a pants-type disposable diaper) as the disposable absorbent article of the present invention is explained referring to FIGS. 4 to 7. However, the present invention is not restricted to the following embodiment.

Figure 4:
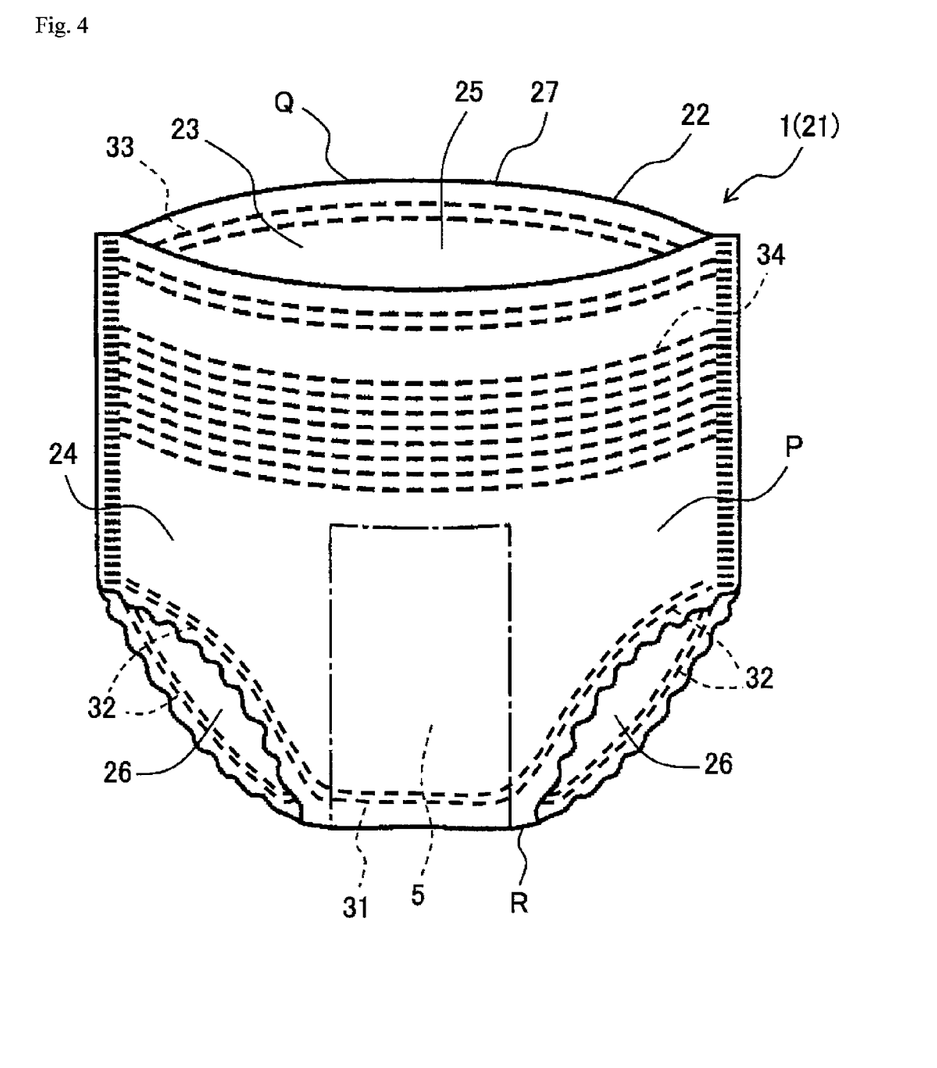
FIG. 4 shows a perspective view of a disposable diaper as the disposable absorbent article of the present invention.
Figure 5:
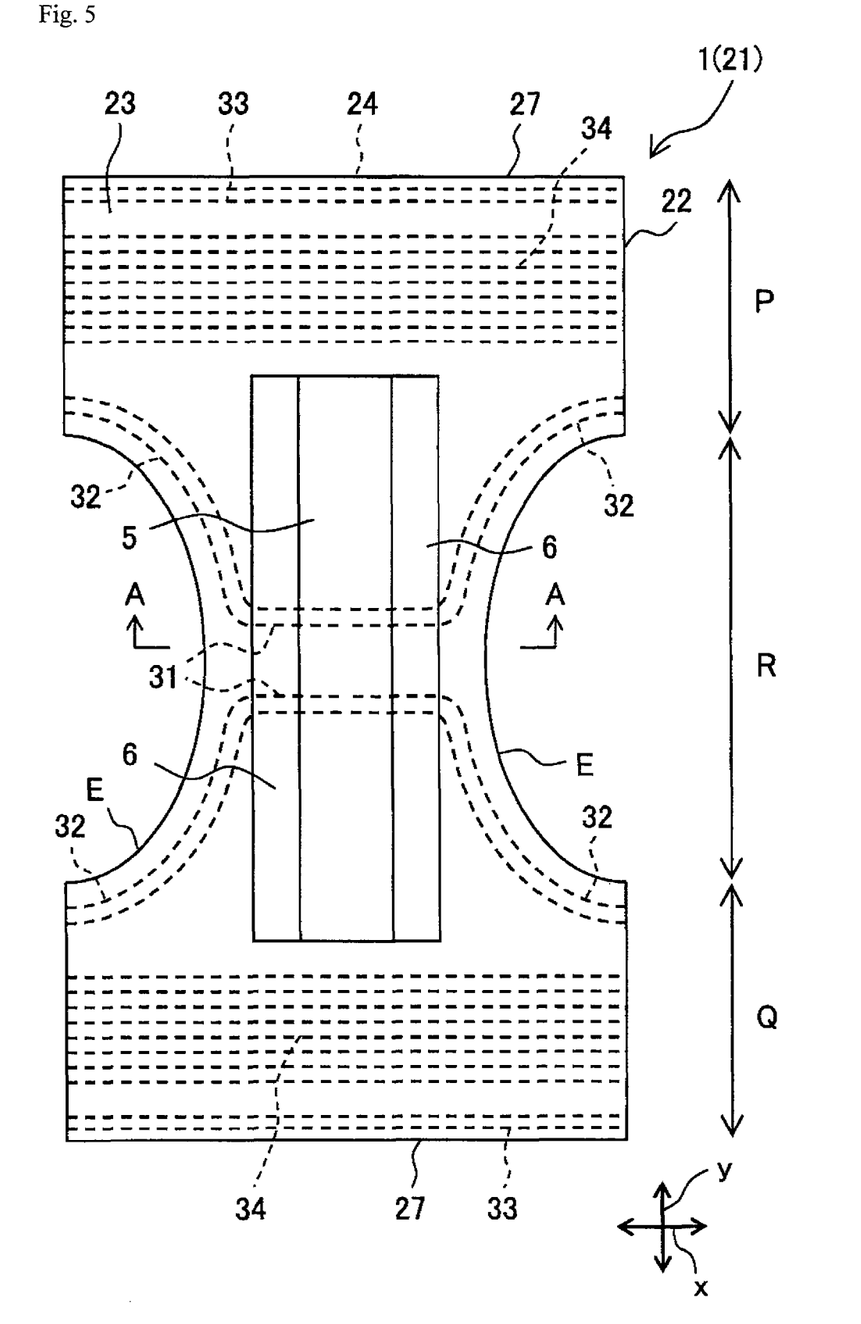
FIG. 5 shows a plan view of the disposable diaper shown in FIG. 4 in a developed state in which a front part and a back part are disjoined.
Figure 6:
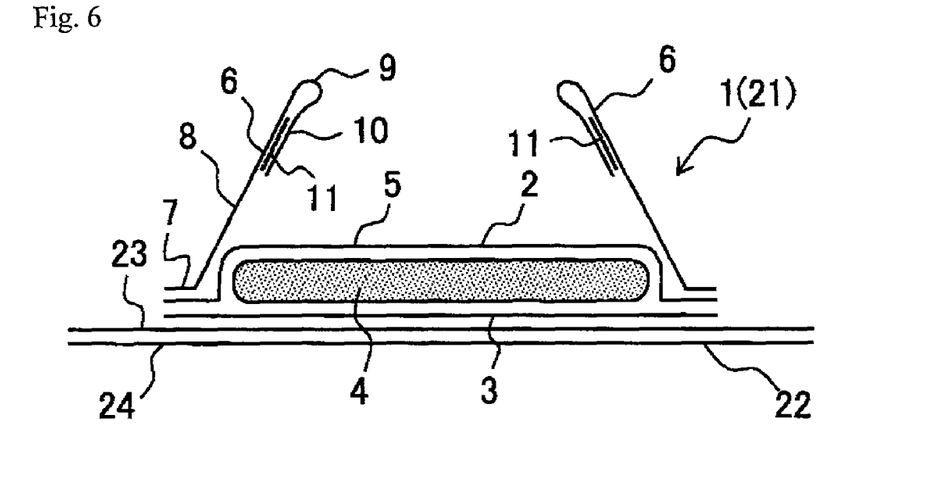
FIG. 6 shows a cross-sectional view taken along the line A-A in FIG. 5.

FIG. 4 shows a perspective view of the disposable diaper as the disposable absorbent article of the present invention. FIG. 5 shows a plan view of the disposable diaper shown in FIG. 4 in a developed state in which the front part and the back part are disjoined. FIG. 6 shows a cross-sectional view taken along the line A-A in FIG. 5.

A disposable diaper 21 has a front part P, a back part Q and a crotch part R situated between the front part P and the back part Q, wherein an absorbent core 4 is provided at the crotch part R. In detail, the disposable diaper 21 comprise a diaper main body 22 having the front part P, the back part Q and the crotch part R, and an absorbent body 5 in which the absorbent core 4 is provided between a top sheet 2 and a back sheet 3, wherein the absorbent body 5 provided with the absorbent core 4 is provided at the crotch part R of the diaper main body 22. The diaper main body 22 has a waist opening 25 and a pair of leg openings 26 which are formed by joining the front part P and the back part Q. The diaper main body 22 is a laminate composed of an inner sheet 23 and an outer sheet 24.

Flaps 6 are provided along edges of opposite sides, with respect to the width direction, of the absorbent core 4 (FIG. 6). The flap 6 has a fixing part 7 joined to the top sheet 2, a rising part 8 extending upward from the fixing part 7, and a fold back part 10 extending from the rising part 8 and formed by folding back the rising part 8 at an upper end 9 of the rising part 8. The rising part 8 and the fold back part 10 are fusion-bonded to each other at a fusion-bond part 11. The rising part 8 and the fold back part 10 of the flap 6 consist of a nonstretch nonwoven fabric which is water-repellent or liquid impermeable. The flaps 6 prevent lateral leakage of urine and the like.

The top sheet 2 of the absorbent body 5 is placed so as to face a wearer's skin at his or her crotch, and allows excrement such as urine and the like to permeate through. The excrement that permeated the top sheet 2 is accommodated in the absorbent core 4. The back sheet 3 is joined to the inner sheet 23 of the diaper main body 22 and prevents the excrement from leaking outside.

A crotch elastic member 31 is disposed so as to extend across the flaps 6, 6 in the width direction x in the crotch part R. In FIG. 5, the crotch elastic member 31 is composed of four elastic members, both ends of two of the elastic members on a front side (a side of the front part P) extend along an edge E of the crotch part R on the front side, and both ends of rest two of the elastic members on a back side (a side of the back part Q) extend along the edge E of the crotch part R on the back side, thereby forming leg elastic members 32 along the entire circumferences of the leg openings 26.

Further, a waist elastic member 33 is disposed along an edge 27 of the waist opening 25, and a body elastic member 34 is disposed in the front part P and the back part Q so as to extend in the width direction x. The respective elastic members are attached between the inner sheet 23 and the outer sheet 24 in a stretched state.

Figure 7:
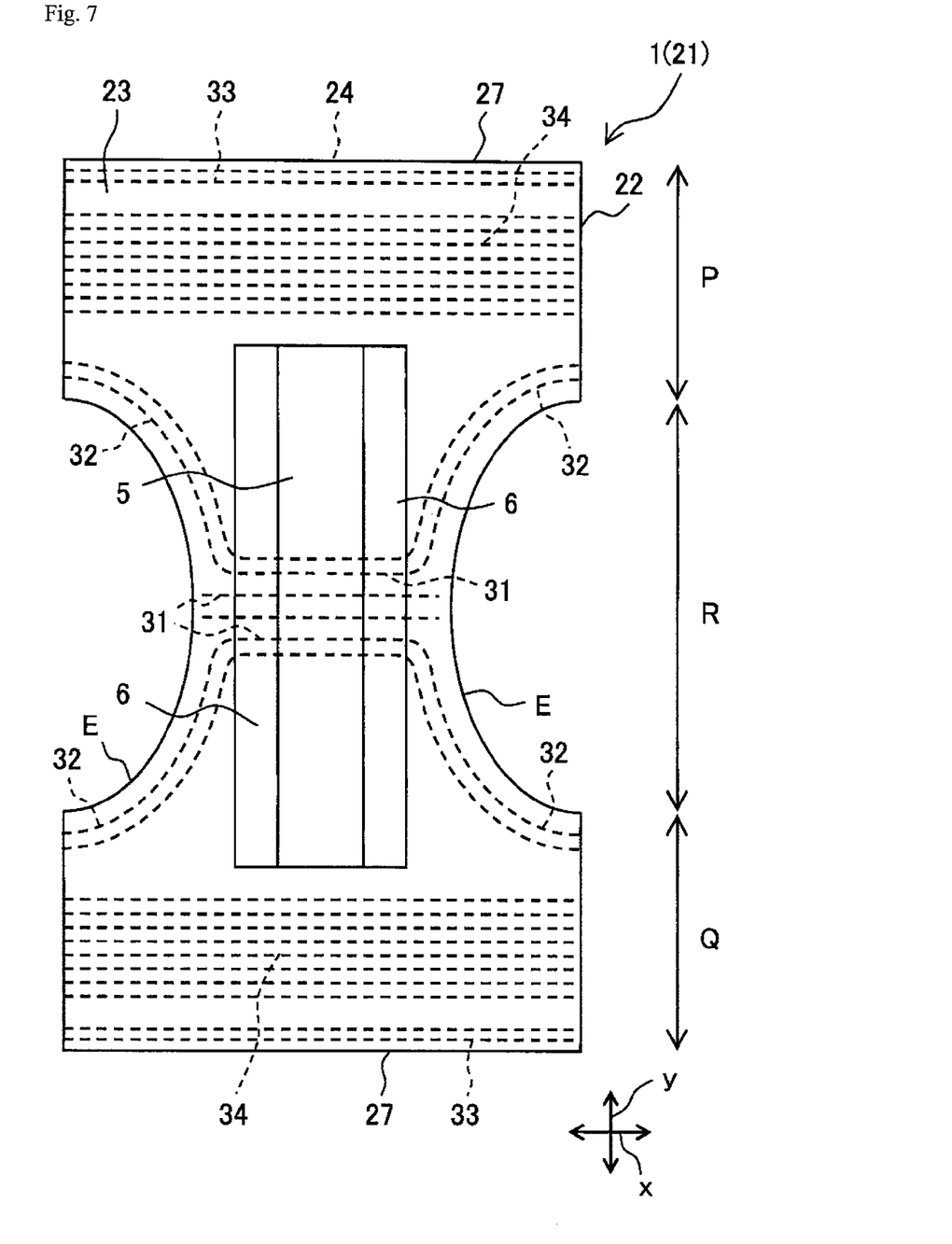
FIG. 7 shows another embodiment of the disposable diaper.

Another embodiment of the crotch elastic member 31 disposed in the disposable diaper 21 is shown in FIG. 7. In FIG. 7, the crotch elastic member 31 is composed of six elastic members, both ends of two of the elastic members on the front side extend along the edge E of the crotch part R on the front side, and both ends of two of the elastic members on the back side extend along the edge E of the crotch part R on the back side. As a result, the leg elastic member 32 is formed along substantially the entire circumferences of the leg openings. Neither ends of two of the elastic members in a middle of the crotch elastic member 31 extend along the edge E of the crotch part R, and the both ends are only disposed so as to extend across the flaps 6, 6 in the width direction x.

As shown in FIG. 7, all elastic member of the crotch elastic member 31 may not extend along the edge E of the crotch part R. Disposing the crotch elastic member 31 and the leg elastic member 32 as shown in FIG. 7 enables to adjust the fit of the flap to a wearer and the fit of the leg openings individually.

The invention claimed is:

1. A disposable absorbent article comprising:
an absorbent body including a top sheet, a back sheet and an absorbent core disposed between the top sheet and the back sheet, and having a longitudinal direction and a width direction; and
a flap provided along an edge of opposite sides in the width direction of the absorbent core; wherein the flap has a fixing part joined to the top sheet and a rising part extending upward from the fixing part, and the rising part consists of a nonstretch nonwoven fabric which is water-repellent or liquid impermeable, and the rising part is not provided with an elastic member.

2. The disposable absorbent article according to claim 1, wherein the flap has a fold back part extending from the rising part and formed by folding back the rising part at an upper end of the rising part, the fold back part consists of a nonstretch nonwoven fabric which is water-repellent or liquid impermeable, and the fold back part is not provided with an elastic member, and the rising part and the fold back part are fusion-bonded to each other at a fusion-bond part.

3. The disposable absorbent article according to claim 2, wherein the fusion-bond part is composed of a group of fusion-bonded lines aligned in the longitudinal direction, and each of the fusion-bonded lines has a shape of a continuous or discontinuous straight line arranged at an angle of from 45° to 135° to the upper end of the rising part.

4. The disposable absorbent article according to claim 2, wherein the disposable absorbent article is a disposable diaper having a front part, a back part and a crotch part situated between the front part and the back part,
the absorbent core is provided at the crotch part, and
an elastic member is disposed so as to extend across the flap in the width direction in the crotch part.

5. The disposable absorbent article according to claim 4, wherein both ends of the elastic member extend along an edge of the crotch part of the disposable diaper.

6. The disposable absorbent article according to claim 2, wherein the rising part and/or the fold back part has a colored portion having a shape of a linear or dots and disposed along the upper end of the rising part.

7. The disposable absorbent article according to claim 1, wherein the disposable absorbent article is a disposable diaper having a front part, a back part and a crotch part situated between the front part and the back part, the absorbent core is provided at the crotch part, and an elastic member is disposed so as to extend across the flap in the width direction in the crotch part.

8. The disposable absorbent article according to claim 7, wherein both ends of the elastic member extend along an edge of the crotch part of the disposable diaper.

9. The disposable absorbent article according to claim 1, wherein the rising part has a colored portion having a shape of a linear or dots and disposed along the upper end of the rising part.

* * * * *